United States Patent
Levitt et al.

(10) Patent No.: US 10,726,202 B2
(45) Date of Patent: Jul. 28, 2020

(54) INCLUSION OF PROTOCOL CONDITIONS WITHIN SEARCH ENGINE RESULTS

(71) Applicant: Bioz, Inc., Los Altos, CA (US)

(72) Inventors: Daniel Levitt, Palo Alto, CA (US); Karin Lachmi, Palo Alto, CA (US); Dan Grunspan, Herzeliya (IL); Ehud Pardo, Mountain View, CA (US)

(73) Assignee: Bioz, Inc., Los Altos, CA (US)

( * ) Notice: Subject to any disclaimer, the term of this patent is extended or adjusted under 35 U.S.C. 154(b) by 576 days.

(21) Appl. No.: 15/483,351

(22) Filed: Apr. 10, 2017

(65) Prior Publication Data
US 2018/0276303 A1     Sep. 27, 2018

Related U.S. Application Data

(60) Provisional application No. 62/475,650, filed on Mar. 23, 2017.

(51) Int. Cl.

| | |
|---|---|
| *G06F 40/205* | (2020.01) |
| *G06F 16/33* | (2019.01) |
| *G06F 16/38* | (2019.01) |
| *G16H 70/20* | (2018.01) |
| *G06F 40/279* | (2020.01) |
| *G06F 40/295* | (2020.01) |

(52) U.S. Cl.
CPC ........ *G06F 40/205* (2020.01); *G06F 16/3331* (2019.01); *G06F 16/38* (2019.01); *G06F 40/279* (2020.01); *G06F 40/295* (2020.01); *G16H 70/20* (2018.01)

(58) Field of Classification Search
CPC .. G06F 17/2705; G06F 16/38; G06F 16/3331; G06F 17/2765; G06F 17/278; G16H 70/20
USPC ......................................................... 707/706
See application file for complete search history.

(56) References Cited

U.S. PATENT DOCUMENTS

2004/0260721 A1 * 12/2004 Coffin ................... G06F 16/211
2009/0138415 A1 *  5/2009 Lancaster ................ G06N 5/04
                                                                706/11

(Continued)

OTHER PUBLICATIONS

Proffitt, Allison. "Bioz Launches Life Sciences Search Engine". Jul. 20, 2016. Bio-IT World. printed pp. 1-2. Accessed date Sep. 16, 2019. http://www.bio-itworld.com/2016/07/20/bioz-launches-life-sciences-search-engine.aspx (Year: 2016).*

*Primary Examiner* — Michael Pham
(74) *Attorney, Agent, or Firm* — Perkins Coie LLP

(57) ABSTRACT

Taught is a search engine for science tools which dynamically evaluates search rank of said science tools through Natural Language Processing and machine learning. The search engine accepts into a corpus of public and private materials, which references individual science tools. Each item of the corpus is evaluated both as to how much that given item should be trusted, and what that item says about individual science tools. Each science tool is evaluated based on what the whole corpus of input data contains concerning those science tools, taking into account how valuable the source of the data is in order to render an overall score and search rank. The search engine generates a judgement of each individual science tool, which is dynamically updated as new information becomes available in the corpus of input data.

22 Claims, 7 Drawing Sheets

(56) References Cited

U.S. PATENT DOCUMENTS

| | | | |
|---|---|---|---|
| 2012/0054240 A1* | 3/2012 | Zhang | G06F 16/382 |
| | | | 707/780 |
| 2012/0066625 A1* | 3/2012 | Encina | G06Q 10/101 |
| | | | 715/765 |
| 2014/0188861 A1* | 7/2014 | Angelo | G06F 16/9535 |
| | | | 707/726 |
| 2016/0026622 A1* | 1/2016 | Bunin | G06F 16/367 |
| | | | 704/9 |

* cited by examiner

INCLUSION OF PROTOCOL CONDITIONS WITHIN SEARCH ENGINE RESULTS

CROSS REFERENCE TO RELATED APPLICATIONS

This patent application claims the benefit of U.S. provisional patent application Ser. No. 62/475,650, filed Mar. 23, 2017, which is incorporated herein by reference in its entirety.

TECHNICAL FIELD

This disclosure is directed to the field of search engines, and more particularly, to providing contextual data for the results of a search.

BACKGROUND

General-purpose search engines have become reasonably good at providing search results, particularly in domains of knowledge that are not highly technical and/or specialized. Some search engines employ "semantic" search techniques that provide contextual meaning and an understanding of searchers' intent, therefore improving search accuracy.

There are also ratings-based search engines where results are filtered as matching a particular rating criteria. The ratings are generated from both objective and subjective criteria, often based on user use reporting. However, these search engines do not take into account the conditions upon which the user reported given statements forming the basis of the rating. In this sense ratings are not put into any form of contextual analysis.

SUMMARY

Introduced are methods and systems that enable efficient and reliable ways provide contextual metadata to search results. A method for generating metadata for a search result of a search engine involves first identifying a use of an object from a collection of searchable data as a search result. The use being one method a user employs the object for. Identification of the use is performed through analysis of contextual data located around a location or hit for the object within the collection of searchable data.

Using the contextual data, the method further identifies a protocol condition for the use. Protocol conditions for the use are conditions described in context associated with references to the object in the collection of searchable data as to how the object was used for the use. Examples of protocol conditions include an amount for the object, a time of use for the object, a frequency of use for the object, a state of matter of the object, a procedure of preparation for the object, a setting for the object, and others.

The searches return metadata for a search result including the object, where the metadata includes a frequency that the protocol condition is found within the corpus of documents with reference to the first object during the first use as compared to one of: all references of the object in the corpus of documents; or all references of the use/context of the object in the corpus of documents.

BRIEF DESCRIPTION OF THE DRAWINGS

These and other objects, features and characteristics of the present embodiments will become more apparent to those skilled in the art from a study of the following detailed description in conjunction with the appended claims and drawings, all of which form a part of this specification. While the accompanying drawings include illustrations of various embodiments, the drawings are not intended to limit the claimed subject matter.

Figure 1:
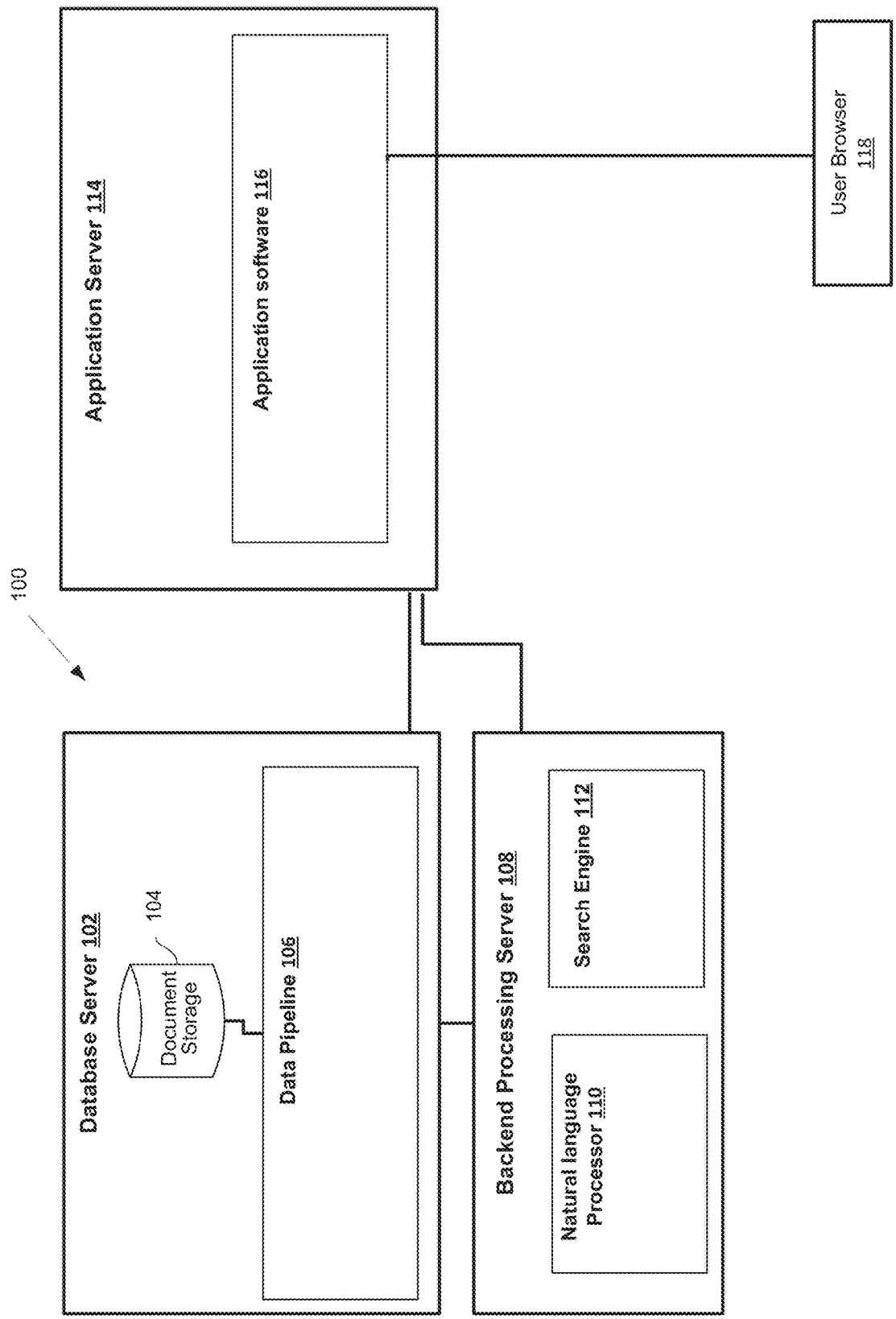
FIG. 1 is a block diagram illustrating an overview of a database server and an evaluation module communicating with servers that display information to a user browser.

The figures depict various embodiments described throughout the Detailed Description for purposes of illustration only. While specific embodiments have been shown by way of example in the drawings and are described in detail below, the invention is amenable to various modifications and alternative forms. The intention, however, is not to limit the invention to the particular embodiments described. Accordingly, the claimed subject matter is intended to cover all modifications, equivalents, and alternatives falling within the scope of the invention as defined by the appended claims.

DETAILED DESCRIPTION

Various embodiments are described herein that relate to systems and methods for extracting metrics from research journals to develop objective rating values for science tools.

In the following description, for the purposes of explanation, numerous specific details are set forth in order to provide a thorough understanding of the embodiments of the invention. One skilled in the art will recognize that the embodiments of the invention may be practiced without these specific details or with an equivalent arrangement. In other instances, well-known structures and devices are shown in block diagram form in order to avoid unnecessarily obscuring the embodiments of the invention.

Brief definitions of terms, abbreviations, and phrases used throughout this application are given below.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described that may be exhibited by some embodiments and not by others. Similarly, various requirements are described that may be requirements for some embodiments but not others.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling or connection between the elements can be physical, logical, or a combination thereof. For example, two devices may be coupled directly or via one or more intermediary channels or devices. As another example, devices may be coupled in such a way that information can be passed there between while not sharing any physical connection with one another. The words "associate with," meanwhile, mean connecting or relating objects, items, etc. For example, a piece of metadata may be associated with a particular legal entity. Additionally, the words "herein," "above," "below," and words of similar import, when used in this application, shall refer to this application as a whole and not to any particular portions of this application. Where the context permits, words in the Detailed Description using the singular or plural number may also include the plural or singular number respectively. The word "or," in reference to a list of two or more items, covers all of the following interpretations of the word: any of the items in the list, all of the items in the list, and any combination of the items in the list.

If the specification states a component or feature "may," "can," "could," or "might" be included or have a characteristic, that particular component or feature is not required to be included or have the characteristic.

The terms "module" and "engine" refer broadly to software, hardware, or firmware components (or any combination thereof). Modules and Engines are typically functional components that can generate useful data or another output using specified input(s). A module may or may not be self-contained. An application program (also called an "application") may include one or more modules, or a module may include one or more application programs.

A computer or a plurality of computers may be, for example, personal computers, mobile phones, PDAs, tablets (e.g., iPad®), or wearable devices (e.g., watches).

The terminology used in the Detailed Description is intended to be interpreted in its broadest reasonable manner, even though it is being used in conjunction with certain examples. The terms used in this specification generally have their ordinary meanings in the art, within the context of the disclosure, and in the specific context where each term is used. For convenience, certain terms may be highlighted, for example using capitalization, italics, and/or quotation marks. The use of highlighting has no influence on the scope and meaning of a term; the scope and meaning of a term is the same, in the same context, whether or not it is highlighted. It will be appreciated that the same element can be described in more than one way.

Consequently, alternative language and synonyms may be used for any one or more of the terms discussed herein, and special significance is not to be placed upon whether or not a term is elaborated on or discussed herein. Synonyms for certain terms are provided. A recital of one or more synonyms does not exclude the use of other synonyms. The use of examples anywhere in this specification, including examples of any terms discussed herein, is illustrative only and is not intended to further limit the scope and meaning of the disclosure or of any exemplified term. Likewise, the disclosure is not limited to various embodiments given in this specification.

A method is performed by one or more computers for extracting metrics from research journals to develop objective rating values for science tools.

FIG. 1 is a block diagram illustrating a system 100. The system 100 includes a database server 102. The database server includes document storage 104 and a data pipeline 106. Document storage 104 is a database storing a large quantity of documents, or "a corpus." An example of a corpus of documents are a collection of published researched journals ranging from a wide array of scientific topics. Another example is a collection of user reviews of a wide array of given products, services, and/or commercial establishments. Communicating with document storage 104 is a data pipeline 106 for communicating the contents of documents to a backend processing server 108 and back again.

The backend processing server 108 includes a natural language processor 110. The natural language processor 110 ("NLP") parses through documents stored in document storage 104 and determines contextual data about words, sentences, and paragraphs therein. The results of the NLP procedure are organized and used by a search engine 112 to generate results from user searches.

The backend server 108 communicates to a front-end server, application server 114. The application server 114 includes application software 116 and interfaces with a user browser 118. The application software 116 handles user requests and forwards to the search engine 112 in order to return results. The configuration of the individual servers and modules is not limited to a single machine or several machines. Various implementations would adjust as most suitable for implementation circumstances or ordinary considerations in the art.

Figure 2:
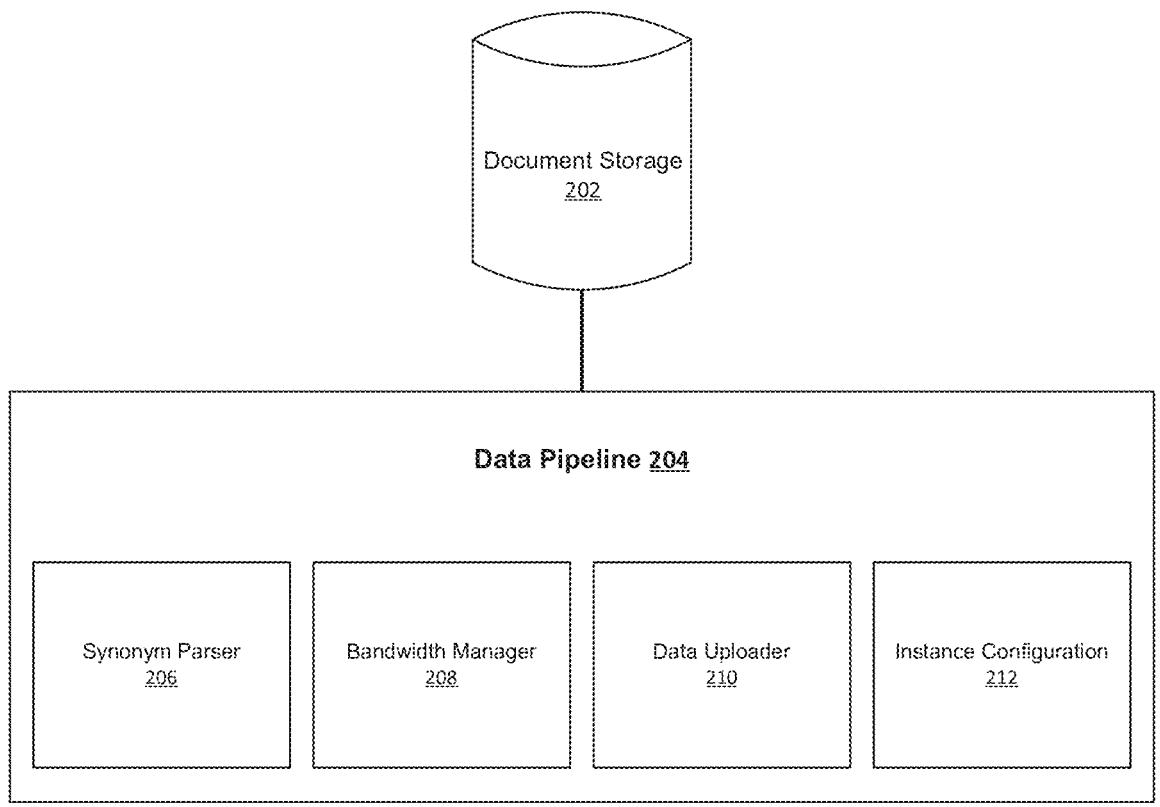
FIG. 2 is a block diagram illustrating a database server consisting of document storage that feeds into a data pipeline.

FIG. 2 is a block diagram illustrating a database server 200 consisting of document storage 202 that feeds into a data pipeline 204. An embodiment of this method receives a corpus of input data to document storage 202. This corpus of input data includes published research journals, patents, grants, published sales data, internally recorded analytical sales data, and published descriptions of scientific experiments. The corpus of input data is mined/parsed for objects used and referenced within. Objects in this case may be a number of things. In some embodiments, these objects are commercial products, services, or locations. A more specific example of such an object is a science tool.

Science tools include laboratory equipment used for taking measurements (e.g., thermometers, graduated cylinders, scales, or spectrometers), equipment for conducting experiments (e.g., Bunsen burners, petri dishes, or microscopes), consumables (e.g., antibodies, assays, or reagents), and resources. These descriptions of scientific experiments and science tools are used in generating the results for said research journals.

Within a data pipeline 204, a synonym parser 206 is responsible for converting all of the different forms of synonym representations to a standard format compatible with the back-end server. Synonym representations may include MeSH (Medical Subject Headings), manually added synonyms, supplements, and company lists. One embodiment takes in one term and converts it into another field that represents all terms that are equivalent to it. This enables the search query to find data on a term, or all of its synonyms, in an efficient way without having to search for all of the synonyms of a term.

A bandwidth manager 208 optimizes the use of the available bandwidth. An embodiment of a bandwidth manager assesses the performance of the systems in terms of data input and output rates, content conversion rates, and computation times. Such embodiments will reallocate resources to improve overall performance of a system.

A data uploader 210 and an instance configuration 212 module exist in the data pipeline to communicate data from the database server 200 to other modules, such as the NLP module of the backend server. The instance configuration 212 module instantiates an object or data, usually categorizing its value, e.g., type or class.

Then, the objects are recorded into a database along with the research journals. Each object is passed into the database with the research document from which it originated.

Figure 3:
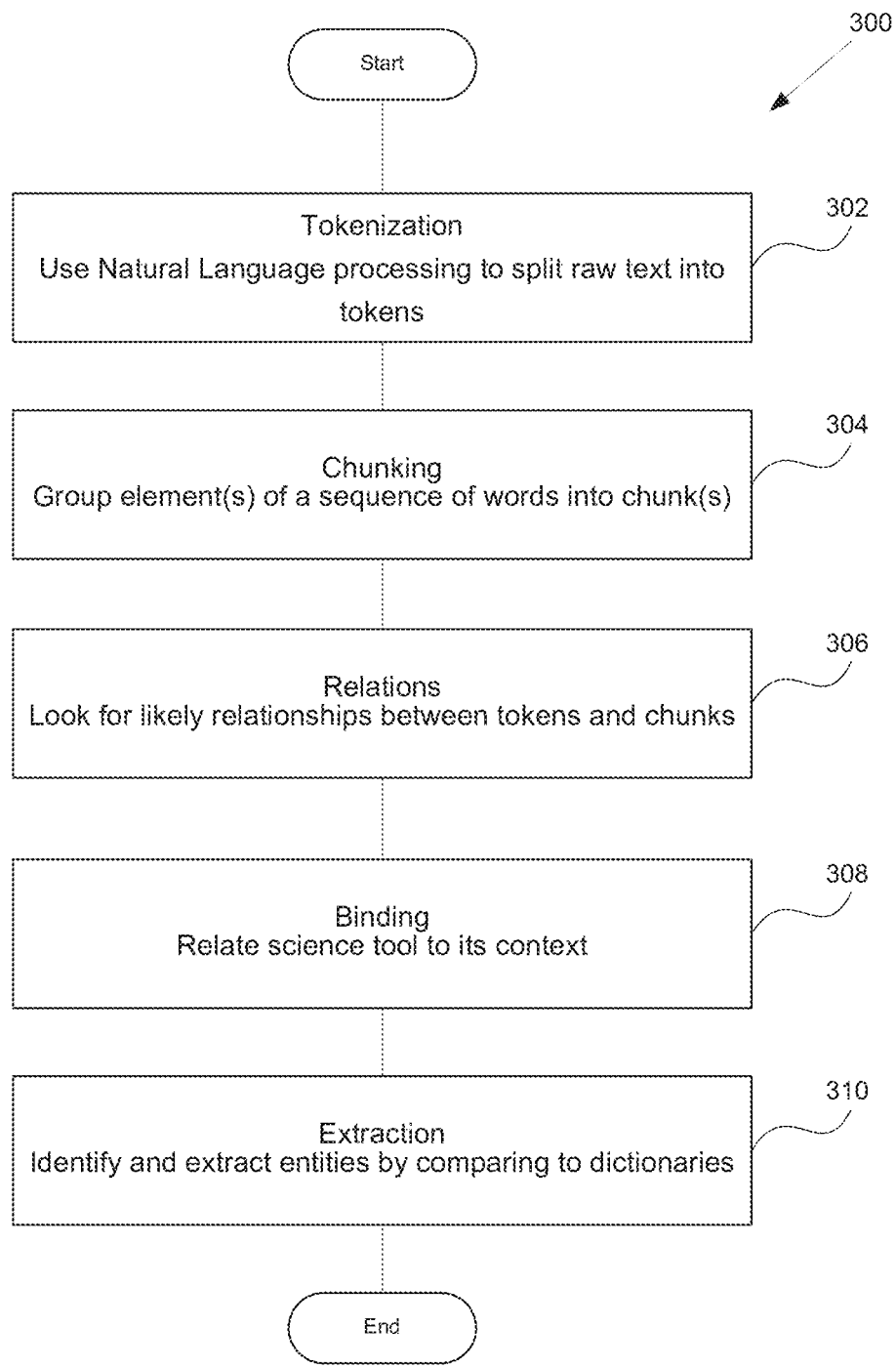
FIG. 3 is a flowchart diagram of an evaluation module consisting of semantic processing engines.

FIG. 3 is a block diagram of an NLP module 300 consisting of the following semantic processing submodules: tokenization 302, chunking 304, relations 306, binding 308, and extraction 310. Note that a journal processing parser can be contained in the NLP module and operates in the same fashion as the other submodules described herein.

First, a plurality of data is collected that pertains to objects by parsing through a corpus of published source data in a journal parser module. The source data is comprised of a corpus of documents. Examples of the documents include any of research journals, research grants and grant proposals, scientific dissertations, patent documents, or consumer reviews. A NLP is used to populate a number of properties for the particular object. NLP is an area of research and application that combines computer science, artificial intelligence, and computational linguistics to understand and manipulate natural language text or speech. A tokenizer module 302 then uses NLP to break a stream of text into words, phrases, symbols or other meaningful elements called tokens.

Next, a chunking module 304 groups elements of a sequence of words into one chunk, without any overlap between obtained groups. Verbs and nouns are identified and their exact offset is marked in the sentence. A domain specific custom chunker is used to tie multiple words into one phrase. Chunkers can identify parts of sentences (e.g. nouns, verbs, adjectives) to determine specific relationships between the words grouped into a chunk. Such examples of a chunking module are noun phrase chunking (NP-chunking) or verb group chunking.

A relations module 306 looks for likely relationships between different entities in the text. A binding module 308 relates each science tool to its context. The module will consider several binding rules. One such rule can bind a product that a company produced to that company. Another rule can bind an assay to its assay name.

A semantic extraction module 310 identifies and extracts entities, facts, attributes, concepts and events. This module enables the analysis of unstructured content via NLP and Named-Entity Recognition (NER). The module contains a knowledge graph and is a superset of dictionaries. Dictionaries are used to identify various types of entities/objects. The set of dictionaries are combinations of collected and edited dictionaries, catalogs from vendors, and public dictionaries in the biology research community such as the MeSH (PubMed) and Gene (NCBI) databases.

A knowledge graph consists of additional sophisticated relationships that are needed to identify entities that are not in the set of dictionaries. The rules comprise company signs, company near location and identifiers of set of signs in text that identify the object as a company. Knowledge Graphs, such as the Knowledge Graph used and marketed by Google, Inc. collect information about objects in the real world and connects that information to related topics. By understanding the relationships between objects, the Knowledge Graph better understands what exactly the user is searching for. The techniques disclosed herein use both dictionaries and a knowledge graph to provide better search results.

After concluding the extraction steps in 310, the properties collected include any of source, conditions, catalog number, dilution, location, temperature, and assay.

Figure 4:
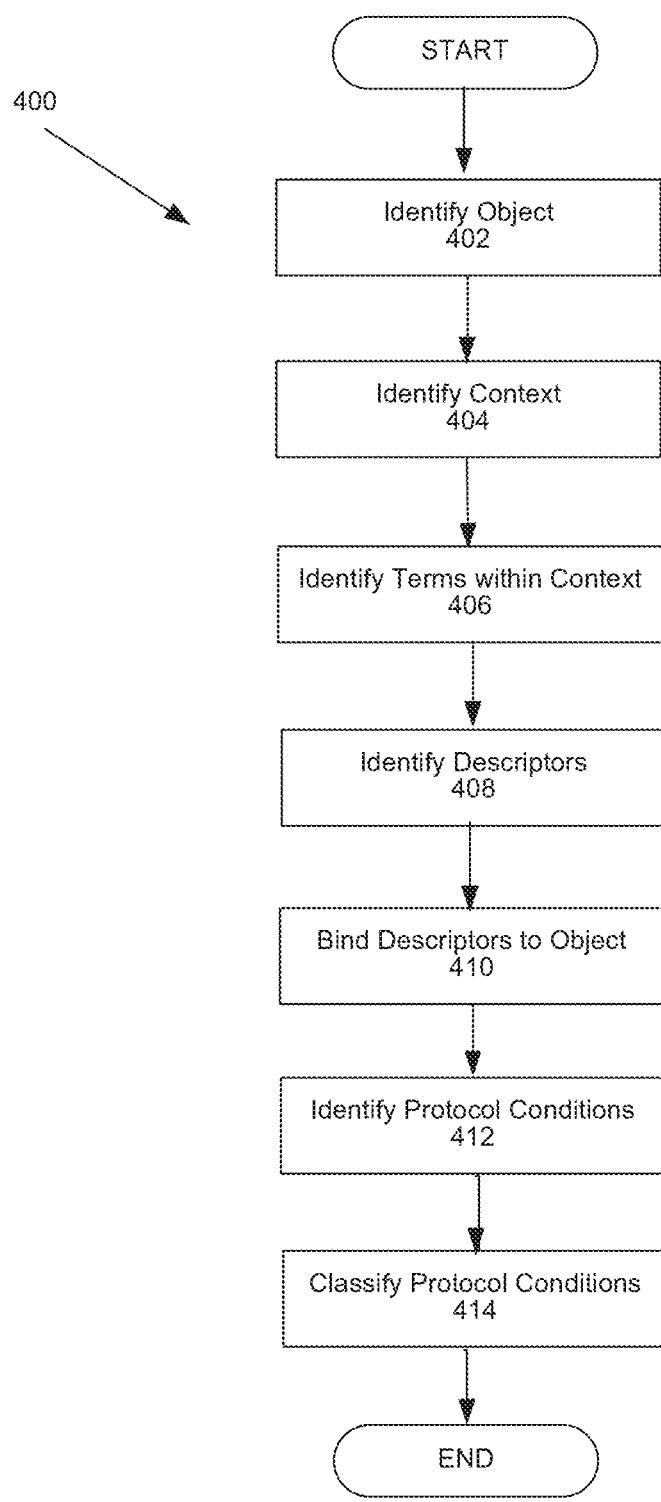
FIG. 4 is a flowchart illustrating the collection of protocol conditions.

FIG. 4 is a flowchart illustrating the collection of protocol conditions. In step 402, the NLP identifies an object. An "object" in this sense is defined as a subject of a context. Objects are often nouns, though could be pictures, or elements of pictures. In the example where the collection of searchable data is one or more research papers, an object may be a reagent used in a particular experiment. In the example where the collection of searchable In step 404, the NLP identifies the extent of the context. The context in this example is the portion of the document that describes the experiment for which the reagent is used. The extent of the context is the portion of the text, images, or multimedia used to describe the experiment. Experiments in research papers are spread over multiple sentences and often take multiple paragraphs. The "context" as described herein is the use of the object. What the object being used for, what the author trying to accomplish with the object, etc.

In step 406, the NLP identifies all terms in each sentence. This distinguishes between terms that are associated with the object, terms that are irrelevant to the object, and transitional terms that merely tie each sentence together. Next the NLP performs a number of object binds. Object binding is a 2 step process. First, in step 408, identifying terms that describe the object and second, in step 410 binding the descriptors to the object. For example: in step 408, the NLP identifies business or commercial entities that are related (e.g., manufacture, sell, offer, market, etc.) to the object. This ties the object to a particular source for the object. In step 410, the NLP binds the entity to the object. Another example for chemical objects is to identify a particular assay of the chemical and bind that assay to the object (chemical). Assay or commercial entity may be specified in same sentences as the object, or in sentences before or in sentences after within the same contextual block. Where the object is a scientific ingredient, step 408 further includes the identification of the assay of the ingredient in addition to the entity or source. Step 410 binds the assay to the ingredient.

Steps 408 and 410 provide additional context to the object. Entity binding provides greater specificity to the identification of the object. In step 412, the NLP identifies terms that describe how the object is used in the context using external dictionaries, tables and a parser. Once these conditions are collected, in step 414 each condition is categorized. Sample categories include: an amount of the object; a dilution of the object; a time of use for the object; a frequency of use for the object; a state of matter of the object; a procedure of preparation for the object; an order of use for the object in the context; a particular assay or enzyme for the object; a setting for the object; or a temperature for the object.

The parser uses external tables that define all protocol conditions, signs and their categories. The parser pre-processes each defined term and generates all permutations and transformations to overcome noise, synonyms and spacing problems to find each in text. The parser includes a set of syntax rules to bind the specific condition to a specific object, made from specific delimiters, keywords and phrases that are common in a corpus of documents, or portion thereof (such as: the materials and methods section of a published journal). The parser further includes an extensive validation phase for each family of protocol conditions. For example: must have a number, size in front. In aggregation the parser also has some rules to combine all equivalent conditions (e.g., 5 h, five hours, 5 hours). Each family of protocol conditions has some predetermined handling to fit within that condition.

Figure 5:
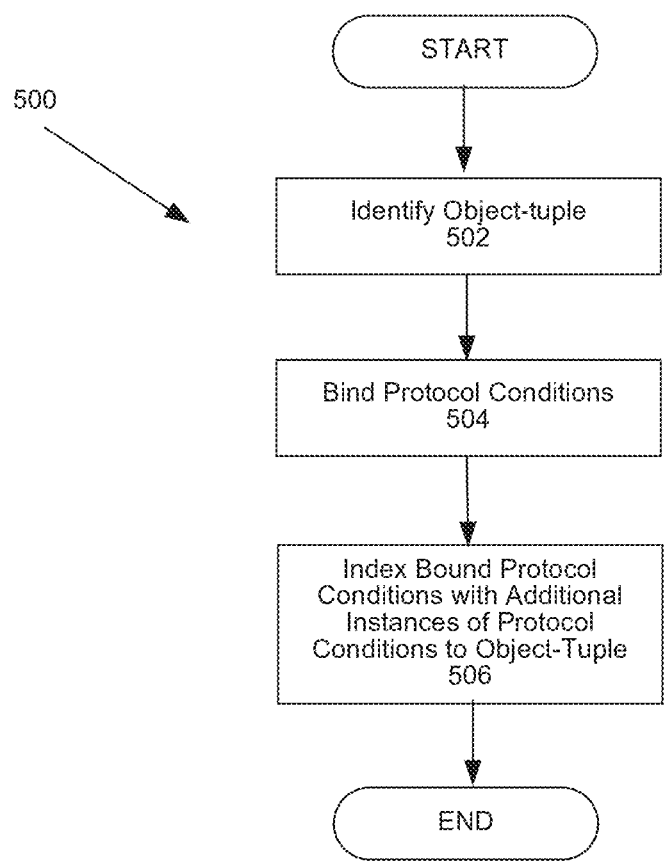
FIG. 5 is a flowchart illustrating binding a protocol condition to a product.

FIG. 5 is a flowchart illustrating binding a protocol condition to a product. In step 502, the backend server or search engine identifies an object tuple. The object-tuple in this case is the object plus the addition of bound descriptors (see step 410 of FIG. 4). An example is a company-object pair, or a company-assay-object triple. A number of descriptors may be involved in each tuple.

In step 504, all categorized protocol conditions related to the object are bound to the object-tuple. The protocol conditions are bounded as metadata to the object-tuple. This binding process is based upon language semantics. A manner of binding is organized based on the category of protocol condition, and the manner in which that protocol condition is used in language to describe the manner of use of the object.

In step 506, the search engine indexes bound protocol conditions for analytics and search. The search engine is enabled to return protocol conditions along with search results (comprising an object tuple). The indexing is categorized by instance of protocol conditions. An instance of a set of protocol conditions is determined by the context in which the given protocol conditions for the object-tuple were found. For example, a given published article or portion thereof may be a single context, and the object-tuple may appear in many contexts (journals, articles, reviews, etc.), each having a list of protocol conditions. A given instance of protocol condition binding is comparable to other instances as comparable or similar (across an entire corpus of documents or other form of a collection of searchable data).

Figure 6:
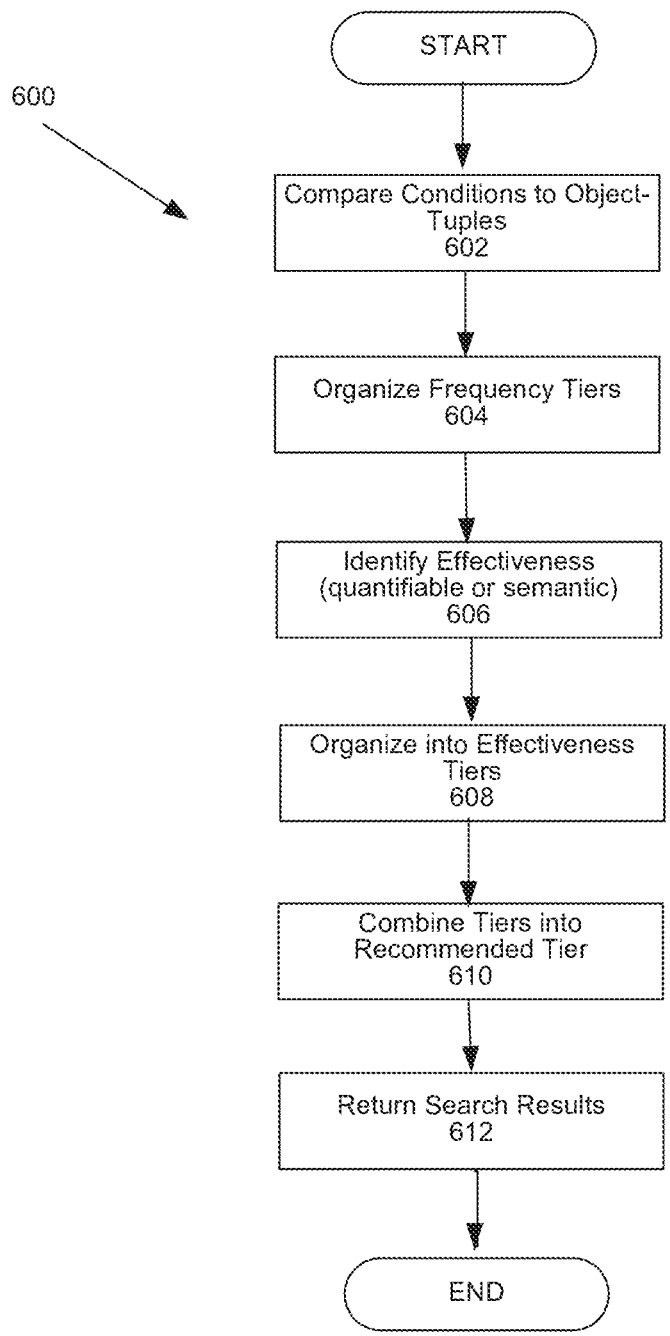
FIG. 6 is a flowchart illustrating derived search analytics from protocol conditions.

FIG. 6 is a flowchart illustrating derived search analytics from protocol conditions. In step 602 the search engine compares a given instance of protocol conditions for a given object-tuple across all instances of protocol conditions for that object-tuple. This comparison lets the search engine determine a frequency that the given protocol condition is found within the corpus of documents with reference to the object-tuple during a given context as compared to all references of the object-tuple in the corpus of documents, or all references of the context of the object-tuple in the corpus of documents.

In step 604, the search engine organizes protocol conditions into tiers of frequency. For example, those conditions that are included greater than 50% of total instances, those conditions included in 30-50% of instances, those conditions included in 20-30% of instances, those conditions included in 5-20% of instance, and those below 5%. Generating tiers for the protocol conditions enables the search engine to provide relevant results to user. A user may specify how many tiers they are interested in seeing using a search engine interface. Results provided from the search engine produce meta data within the frequency tiers that are requested.

In step 606. The NLP additionally identifies "effectiveness" as connected to a given protocol condition. Effectiveness is determined differently depending on the kind of object and the context involved. Where a reagent (object) is used in a reaction (context), the output of the reaction, provides a quantifiable effectiveness and is reported (identifiable by the NLP) in each document discussing the use of the object in the context. This method of associating an effectiveness to a protocol condition is based on correlation. While a given protocol condition may not be solely responsible for a particular effectiveness, the data helps users generate useful hypotheses in selecting a manner of use. The search engine is enabled to identify trends of given protocol conditions to results.

In some cases a quantifiable effectiveness is not readily available. Where a food (object) is consumed for dinner (context) the effectiveness is less quantifiable. In this example, an suitable sample protocol condition is "use of hot sauce." The user may semantically use laudatory words, negative words, or none at all. In this manner, the NLP may, at minimum, generate a binary effectiveness statistic. In some embodiments, the word choice of the user may be sub-divided into tiers (e.g., some words being more laudatory than others).

In step 608, the effectiveness is correlated with the appearance frequency of a given protocol condition. Whereby protocol conditions are additionally sub-divided into effectiveness tiers in parallel with the frequency tiers. Thus, those protocol conditions that appear in the highest frequency in instances of high effectiveness are sorted into higher tiers while those protocol conditions that appear in high frequency in instances of low effectiveness are sorted into lower tiers.

In step 610, the search engine combines both the effectiveness tiers and the frequency tiers into a single recommended set of protocol conditions. In this step each of the tiers are combined and averaged. Those protocol conditions that appear in both high frequency tiers and high effectiveness tiers are placed into a high recommendation tier. For example, if there are five tiers for each measurement, a score for each is added, and then divided by the number of measurements. The remaining score places the protocol condition into a final recommendation tier.

It is understood that through routine experimentation, a given measurement (e.g., frequency tiers or effectiveness tiers) are more effective than others. In this case, during combination, a given tier may be weighted more than another. In certain cases, an entire measurement may be discarded (e.g., perhaps the reliability of the effectiveness of generic hot sauce on a food item is unclear or not specific enough).

In step 612, the search engine presents results. Where a user searches for a given object, results may include several object-tuples (e.g., where a given object may be purchased from more than one entity). In accessing a given search result, the search engine returns the metadata on the protocol conditions as organized by the recommendation tiers.

In some embodiments, the method described in FIG. 6 pertains merely to objects rather than object-tuples (as described above). The search engine thereby Aggregates for statistical purposes across every instance of an object rather than across of instances of bound objects including further restrictive descriptors (e.g., use, source, assay, etc.). This leads to fewer records generated as many instances of given object-tuples are folded together into a single object.

An example process follows:

First an NLP receives a text associated with a corpus of documents (e.g., a collection of research journals). Next, the NLP identifies sentences or isolated blocks from the text. The NLP further identifies objects (e.g., science tools) from terms within each of the sentences. Then the NLP identifies an use or context (e.g., an experiment) discussed by the text that the science tools were used in.

The NLP binds each object to the associated context in order to generate object-use pairs. Further identified by the NLP are each of the conditions mentioned in the text using external dictionaries, tables and a parser, the conditions are identified as associated with object-use pairs and are sorted into categories. The search engine generates records wherein each record includes an object-use-condition tuple. Given the tuples, the search engine aggregates all object-use-condition tuples identified across every text across the corpus of documents. The search engine receives user queries for objects and then returns a search result including the object and metadata of the aggregated object-use-condition tuples.

An Example Machine Overview

The machine-implemented operations described above can be implemented at least partially by programmable circuitry programmed/configured by software and/or firmware, or entirely by special-purpose circuitry, or by a combination of such forms. Such special-purpose circuitry (if any) can be in the form of, for example, one or more application-specific integrated circuits (ASICs), programmable logic devices (PLDs), field-programmable gate arrays (FPGAs), system-on-a-chip systems (SOCs), etc.

Software or firmware to implement the embodiments introduced here may be stored on a machine-readable storage medium and may be executed by one or more general-purpose or special-purpose programmable microprocessors. A "machine-readable medium," as the term is used herein, includes any mechanism that can store information in a form accessible by a machine (a machine may be, for example, a computer, network device, cellular phone, personal digital assistant (PDA), manufacturing tool, any device with one or more processors, etc.). For example, a machine-accessible medium includes recordable/non-recordable media (e.g., read-only memory (ROM); random access memory (RAM); magnetic disk storage media; optical storage media; flash memory devices; etc.), etc.

Figure 7:
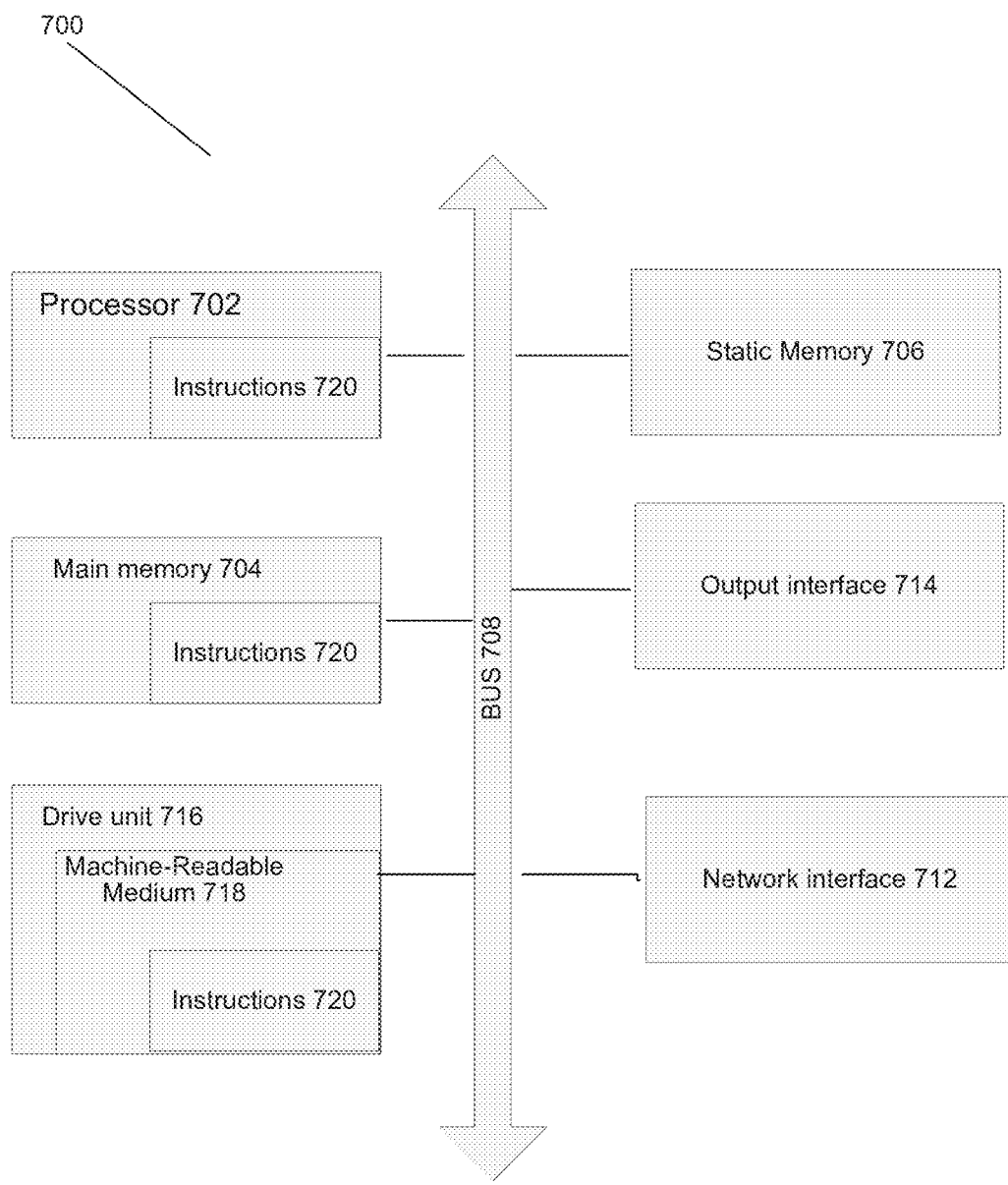
FIG. 7 is a block diagram of an exemplary computer system.

FIG. 7 is a block schematic diagram of a system in the exemplary form of a computer system 700 within which a set of instructions for causing the system to perform any one of the foregoing methodologies and logical flows may be executed. In alternative embodiments.

The computer system 700 includes a processor 702, a main memory 704 and a static memory 706, which communicate with each other via a bus 708. The computer system 700 further includes a network interface 712. The computer system 700 also includes an output interface 714, for example, a USB interface, a network interface, or electrical signal connections and/or contacts;

The disk drive unit 716 includes a machine-readable medium 718 on which is stored a set of executable instructions, i.e. software 720, embodying any one, or all, of the methodologies described herein. The software 720 is also shown to reside, completely or at least partially, within the main memory 704 and/or within the processor 702. The software 720 may further be transmitted or received over a network by means of a network interface device 714.

In contrast to the system 700 discussed above, a different embodiment uses logic circuitry instead of computer-executed instructions to implement processing entities. Depending upon the particular requirements of the application in the areas of speed, expense, tooling costs, and the like, this logic may be implemented by constructing an application-specific integrated circuit (ASIC) having thousands of tiny integrated transistors. Such an ASIC may be implemented with CMOS (complementary metal oxide semiconductor), TTL (transistor-transistor logic), VLSI (very large systems integration), or another suitable construction. Other alternatives include a digital signal processing chip (DSP), discrete circuitry (such as resistors, capacitors, diodes, inductors, and transistors), field programmable gate array (FPGA), programmable logic array (PLA), programmable logic device (PLD), and the like.

It is to be understood that embodiments may be used as or to support software programs or software modules executed upon some form of processing core (such as the CPU of a computer) or otherwise implemented or realized upon or within a system or computer readable medium. A machine-readable medium includes any mechanism for storing or transmitting information in a form readable by a machine, e.g. a computer.

The computer-readable media may include non-transitory computer-readable storage media, which may include hard drives, floppy diskettes, optical disks, CD-ROMs, DVDs, read-only memories (ROMs), random access memories (RAMs), EPROMs, EEPROMs, flash memory, magnetic or optical cards, solid-state memory devices, or other types of storage media suitable for storing electronic instructions. In addition, in some implementations, the computer-readable media may include a transitory computer-readable signal (in compressed or uncompressed form). Examples of computer-readable signals, whether modulated using a carrier or not, include, but are not limited to, signals that a computer system hosting or running a computer program can be configured to access, including signals downloaded through the Internet or other networks. Finally, the order in which the operations are described is not intended to be construed as a limitation, and any number of the described operations can be combined in any order and/or in parallel to implement the process.

REMARKS

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling others skilled in the relevant art to understand the claimed subject matter, the various embodiments, and the various modifications that are suited to the particular uses contemplated.

While embodiments have been described in the context of fully functioning computers and computer systems, those skilled in the art will appreciate that the various embodiments are capable of being distributed as a program product in a variety of forms and that the disclosure applies equally regardless of the particular type of machine or computer-readable media used to actually affect the distribution.

Although the above Detailed Description describes certain embodiments and the best mode contemplated, no matter how detailed the above appears in text, the embodiments can be practiced in many ways. Details of the systems and methods may vary considerably in their implementation details while still being encompassed by the specification. As noted above, particular terminology used when describing certain features or aspects of various embodiments should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless those terms are explicitly defined herein. Accordingly, the actual scope of the invention encompasses not only the disclosed embodiments, but also all equivalent ways of practicing or implementing the embodiments under the claims.

The language used in the specification has been principally selected for readability and instructional purposes, and it may not have been selected to delineate or circumscribe the inventive subject matter. It is therefore intended that the scope of the invention be limited not by this Detailed Description, but rather by any claims that issue on an application based hereon. Accordingly, the disclosure of various embodiments is intended to be illustrative, but not limiting, of the scope of the embodiments, which are set forth in the following claims.

The invention claimed is:

1. A method for parsing a corpus of documents in order to generate results for a search engine results comprising:
   receiving, by a natural language processor, a text associated with a corpus of documents;
   identifying, by the natural language processor, sentences from the text;
   identifying, by the natural language processor, science tools from terms within each of the sentences, science tools include any of:
      laboratory equipment used for taking measurements;
      equipment for conducting experiments;
      consumables; and
      experiment resources;
   identifying, by the natural language processor, an experiment discussed by the text that the science tools were used in;
   binding, by the natural language processor, each science tool to the associated experiment in order to generate tool-experiment pairs;
   identifying, by the natural language processor, each condition mentioned in the text using external dictionaries, tables and a parser, the conditions are identified as associated with tool-experiment pairs and are sorted into categories including:
      an amount for the science tool;
      a dilution for the science tool;
      a time of use for the science tool;
      a frequency of use for the science tool;
      a state of matter of the science tool;
      a procedure of preparation for the science tool;
      an order of use for the science tool in the scientific experiment;
      a particular assay for the science tool;
      a setting for the science tool; or
      a temperature for the science tool;
   generating, by the natural language processor, tool-experiment-condition tuples that each comprise a tool-experiment pair and a condition associated with the tool-experiment pair;
   generating, by a search engine, records wherein each record includes one of the generated tool-experiment-condition tuple;
   aggregating, by a search engine, all tool-experiment-condition tuples identified across every text across the corpus of documents;
   receiving, by the search engine, a search request for a given science tool; and
   returning, by the search engine, a search result including the science tool and metadata of the aggregated tool-experiment-condition tuples.

2. A method for generating metadata for a search result of a search engine comprising:
   identifying, by a natural language processor, a first use of a first object, the first object is included in a corpus of documents, wherein the corpus of documents is searchable by a search engine and the first object is a potential search result associated with a plurality of search queries in the search engine, the first use is one method a user employs the first object for, identification of the first use is through analysis, by the natural language processor, of contextual data in the corpus of documents associated with the first object;
   identifying, by the natural language processor, a first protocol condition for the first use, the first protocol condition for the first use including a condition described in context associated with references to the first object in the corpus of documents as to how the first object was used for the first use; and
   returning, by a search engine, metadata for a search result including the first object, the metadata including a frequency that the first protocol condition is found within the corpus of documents with reference to the first object during the first use, the frequency defined as a number of instances, in the corpus of documents, in which the first protocol condition occurs with reference to the first object during the first use, as a percentage of one of:
      a number of all references of the first object in the corpus of documents; or
      a number of all references of the first use of the first object in the corpus of documents.

3. The method of claim 2, wherein the first object is a science tool and the first use is a scientific experiment.

4. The method of claim 3, wherein the first protocol condition is any of:
   an amount for the science tool;
   a dilution for the science tool;
   a time of use for the science tool;
   a frequency of use for the science tool;
   a state of matter of the science tool;
   a procedure of preparation for the science tool;
   an order of use for the science tool in the scientific experiment;
   a particular assay for the science tool;
   a setting for the science tool; or
   a temperature for the science tool.

5. The method of claim 3, wherein the corpus of documents is a collection of published scientific journals.

6. The method of claim 2, wherein said returning further comprises:
   rendering for a display, by a graphic user interface, a link positioned adjacent to the search result, the link directing the graphic user interface a screen presenting the metadata.

7. The method of claim 3, said identifying the first protocol condition further comprising:
   identifying, by the natural language processor, a measured experiment result of the scientific experiment, the measured experiment result pertaining to the first protocol condition.

8. The method of claim 7, wherein the metadata further includes other protocol conditions associated with the first object during the first use, and said returning further comprising:
   sorting, by the search engine, the first protocol condition amongst the other protocol conditions within the metadata into a relevance rank based on a comparison of the measured experiment result of the first protocol condition to a number of other measured experiment results each associated with the other protocol conditions.

9. The method of claim 2, wherein the corpus of documents is a plurality of user written reviews collected concerning a commercial establishment or a consumer product.

10. The method of claim 3, further comprising:
identifying, by the natural language processor, a first sales entity for the first object, the first sales entity is a corporate entity that sells and markets the first object; and
binding as searchable data for the search engine, by the natural language processor, the first sales entity to the first object.

11. The method of claim 10, further comprising:
returning, by a search engine, additional metadata for the search result including the first object, the additional metadata including a frequency that the first sales entity is found within the corpus of documents with reference to the first object during the first use as compared to one of:
all references of the first object in the corpus of documents; or
all references of the first use of the first object in the corpus of documents.

12. The method of claim 2, further comprising:
receiving, at the search engine, from a user device, a query relating to the first object;
outputting, by the search engine, for display by the user device, a set of search results including the first object and the metadata associated with the search result for the first object.

13. The method of claim 12, further comprising:
returning metadata for another search result for the first object, the metadata for the other search result including a frequency that a second protocol condition is found within the corpus of documents with reference to the first object during the first use, the frequency defined as a number of instances, in the corpus of documents, in which the second protocol condition occurs with reference to the first object during the first user, as a percentage of one of:
the number of all references of the first object in the corpus of documents; or
the number of all references of the first use of the first object in the corpus of documents;
wherein the set of search results further includes the first object and the metadata for the other search result; and
organizing the set of search results based on the frequency that the first protocol condition is found within the corpus of documents and the frequency that the second protocol condition is found within the corpus of documents.

14. A system for generating metadata for a search result of a search engine comprising:
a natural language processor having instructions stored in a non-transitory computer readable storage medium that when executed cause the natural language processor to identify a first use of a first object, the first object is included in a corpus of documents, wherein the corpus of documents is searchable by a search engine and the first object is a potential search result associated with a plurality of search queries in the search engine, the first use is one method a user employs the first object for, identification of the first use is through analysis, by the natural language processor, of contextual data in the corpus of documents associated with the first object, the natural language processor further configured to identify a first protocol condition for the first use, the first protocol condition for the first use including a condition described in context associated with references to the first object in the corpus of documents as to how the first object was used for the first use; and
a search engine communicatively coupled to the natural language processor, the search engine having instructions stored in a non-transitory computer readable storage medium that when executed cause the search engine to return metadata for a search result including the first object, the metadata including a frequency that the first protocol condition is found within the corpus of documents with reference to the first object during the first use, the frequency defined as a number of instances, in the corpus of documents, in which the first protocol condition occurs with reference to the first object during the first use, as a percentage of one of:
a number of all references of the first object in the corpus of documents; or
a number of all references of the first use of the first object in the corpus of documents.

15. The system of claim 14, wherein the first object is a science tool and the first use is a scientific experiment.

16. The system of claim 15, wherein the first protocol condition is any of:
an amount for the science tool;
a dilution for the science tool;
a time of use for the science tool;
a frequency of use for the science tool;
a state of matter of the science tool;
a procedure of preparation for the science tool;
an order of use for the science tool in the scientific experiment;
a particular assay for the science tool;
a setting for the science tool; or
a temperature for the science tool.

17. The system of claim 15, wherein the corpus of documents is a collection of published scientific journals.

18. The system of claim 14, further comprising:
a graphic user interface configured to render, for a display, a link positioned adjacent to the search result, the link directing the graphic user interface a screen presenting the metadata.

19. The system of claim 15, wherein the natural language processor is further configured to identify, with respect to the first protocol condition, a measured experiment result of the scientific experiment, the measured experiment result pertaining to the first protocol condition.

20. The system of claim 19, wherein the metadata further includes other protocol conditions associated with the first object during the first use, and the search engine further configured to sort the first protocol condition amongst the other protocol conditions within the metadata into a relevance rank based on a comparison of the measured experiment result of the first protocol condition to a number of other measured experiment results each associated with the other protocol conditions.

21. The system of claim 14, wherein the corpus of documents is a plurality of user written reviews collected concerning a commercial establishment or a consumer product.

22. The system of claim 15, where the natural language processor is further configured to identify a first sales entity for the first object, the first sales entity is a corporate entity that sells and markets the first object, and bind as searchable data for the search engine the first sales entity to the first object.

* * * * *